United States Patent
Chen et al.

(10) Patent No.: US 10,059,700 B2
(45) Date of Patent: Aug. 28, 2018

(54) SUPPORTED CATALYST FOR ALDEHYDE COUPLING REACTION, METHOD FOR PERFORMING ALDEHYDE COUPLING REACTION, AND METHOD FOR REGENERATING SUPPORTED CATALYST FOR ALDEHYDE COUPLING REACTION

(71) Applicants: SEKISUI CHEMICAL CO., LTD., Osaka (JP); Colorado State University Research Foundation, Fort Collins, CO (US)

(72) Inventors: Eugene Y. X. Chen, Fort Collins, CO (US); Lu Wang, Fort Collins, CO (US); Yuji Eguchi, Tsukuba (JP)

(73) Assignees: SEKISUI CHEMICAL CO., LTD., Osaka (JP); COLORADO STATE UNIVERSITY RESEARCH CORPORATION, Fort Collins, CO (US)

( * ) Notice: Subject to any disclaimer, the term of this patent is extended or adjusted under 35 U.S.C. 154(b) by 0 days.

(21) Appl. No.: 15/168,594

(22) Filed: May 31, 2016

(65) Prior Publication Data
US 2016/0346774 A1 Dec. 1, 2016

Related U.S. Application Data

(60) Provisional application No. 62/168,923, filed on Jun. 1, 2015.

(51) Int. Cl.

| | | |
|---|---|---|
| B01J 29/04 | (2006.01) | |
| C07D 307/02 | (2006.01) | |
| C07D 407/06 | (2006.01) | |
| B01J 21/08 | (2006.01) | |
| B01J 31/02 | (2006.01) | |
| B01J 31/40 | (2006.01) | |
| B01J 31/06 | (2006.01) | |
| B01J 35/02 | (2006.01) | |

(52) U.S. Cl.
CPC ............ *C07D 407/06* (2013.01); *B01J 21/08* (2013.01); *B01J 31/0218* (2013.01); *B01J 31/0244* (2013.01); *B01J 31/0254* (2013.01); *B01J 31/0271* (2013.01); *B01J 31/06* (2013.01); *B01J 31/40* (2013.01); *B01J 35/023* (2013.01); *B01J 2231/341* (2013.01); *Y02P 20/584* (2015.11)

(58) Field of Classification Search
CPC ....... C07D 407/06; B01J 31/028; B01J 31/06; B01J 31/0254; B01J 31/0244; B01J 31/0271; B01J 31/40; B01J 21/16; B01J 21/08; B01J 38/60; B01J 2231/341; Y02P 20/584
USPC ..... 549/473, 497; 502/62, 80, 401; 568/331, 568/315
See application file for complete search history.

(56) References Cited

U.S. PATENT DOCUMENTS

| | | | |
|---|---|---|---|
| 5,831,097 A | 11/1998 | Ebel et al. | |
| 6,673,737 B2 | 1/2004 | Mehnert et al. | |
| 2007/0021615 A1 | 1/2007 | Kohler et al. | |
| 2014/0005415 A1 | 1/2014 | Sun et al. | |

FOREIGN PATENT DOCUMENTS

| | | | |
|---|---|---|---|
| GB | 2427192 | * | 12/2006 |
| JP | 05253490 | | 10/1993 |
| JP | 2007501815 | | 2/2007 |
| JP | 2008266297 | | 11/2008 |
| JP | 2014034021 | | 2/2014 |

OTHER PUBLICATIONS

Wikipedia, Potassium ter-butoxide, Sep. 2014, p. 1-3 (Year: 2014).*
Storey et al., "Imidazole based solid-supported catalysts for the benzoin condensation," Tetrahedron Letters 46, 2005, pp. 7337-7339.
Castells et al., "Postulation of bis(thiazolin-2-ylidene)s as the catalytic species in the benzoin condensation catalyzed by a thiazolium salt plus base," J. Org. Chem, 53, 1988, pp. 4433-4436.
Castells et al., "Insoluble polymer-supported conjugate bases of thiazolium ions as catalysts in organic chemistry," Israel Journal of Chemistry, 1978, vol. 17, pp. 278-283.
Hamaya et al., "Benzoin Condensation Catalyzed by Azolium Salt in Water," Abstracts of papers Congress of Heterocyclic Chemistry, Sep. 10, 2000, 31th, pp. 15-16.
Bortolini et al., "Thiazolium-functionalized polystyrene monolithic microreators for continuous-flow umpolung catalysis," Green Chemistry, 2013, vol. 15, pp. 2981-2992.
Estager et al., "Neat benzoin condensation in recyclable room-temperature ionic liquids under ultrasonic activation," Tetrahedron Letters, 2007, vol. 48, pp. 755-759.
Iwamoto et al., "Benzoin reaction in water as an aqueous medium catalyzed by benzimidazolium salt," Tetrahedron Letters, 2006, vol. 47, pp. 7175-7177.
International Search Report in respect to International Application No. PCT/JP2016/066979, dated Jul. 19, 2016.
Shylesh et al., "Sustainable, green protocols for heterogenized organocatalysts: N-phenylthiazolium salts heterogenized on organic-inorganic hybrid mesoporous supports," Journal of Molecular Catalysis A: Chemical, 2010, vol. 332, pp. 65-69.

* cited by examiner

*Primary Examiner* — Taylor V Oh
(74) *Attorney, Agent, or Firm* — Greenblum & Bernstein, P.L.C.

(57) ABSTRACT

A supported catalyst for aldehyde coupling reaction, comprising a carrier having supported thereon a catalyst comprising at least one azolium compound selected from the group consisting of a thiazolium salt, an imidazolium salt, a benzimidazolium salt and a triazolium salt, the azolium compound having, at a nitrogen atom thereof, a substituent selected from the group consisting of an aliphatic group having 6 or more carbon atoms and an aromatic group having 6 or more carbon atoms.

10 Claims, No Drawings

SUPPORTED CATALYST FOR ALDEHYDE COUPLING REACTION, METHOD FOR PERFORMING ALDEHYDE COUPLING REACTION, AND METHOD FOR REGENERATING SUPPORTED CATALYST FOR ALDEHYDE COUPLING REACTION

This application claims the benefit of U.S. Provisional Application No. 62/168,923, filed Jun. 1, 2015, the entire content of which is incorporated herein by reference in its entirety.

TECHNICAL FIELD

The present invention relates to a supported catalyst for aldehyde coupling reaction, a method for performing an aldehyde coupling reaction, and a method for regenerating a supported catalyst for aldehyde coupling reaction.

DESCRIPTION OF RELATED ART

Azolium compounds such as a thiazolium salt, an imidazolium salt and a triazolium salt are known to be used as catalysts for aldehyde coupling reactions such as benzoin condensation (see, for example, Patent Document 1 and Non-patent Document 1). However, these azolium compounds are difficult to recover and, hence, the industrial use as catalysts of the compounds as such is difficult. For this reason, it is practiced to use the azolium compounds in the form of supported catalysts using organic or inorganic carriers. For example, the supported catalysts proposed include a catalyst comprised of an imidazolium salt supported on polystyrene (Non-patent Document 2), a catalyst comprised of a thiazolium salt supported on polystyrene (Non-patent Document 3), a thiazolium salt or an imidazolium salt which is immobilized on an inorganic oxide such as silica through an alkoxysilane (Patent Documents 2 to 4), and an imidazolium salt as ionic liquid which is immobilized on a smectite clay such as montmorillonite (Patent Document 5).

However, these supported catalysts each comprised of an azolium compound supported on a carrier have problems such as insufficient yield of targeted acyloin, lowering of catalyst activity within a relatively short period of time, and poor recyclability.

DOCUMENTS OF RELATED ART

Patent Document

[Patent Literature 1] U.S. Pat. No. 5,831,097
[Patent Literature 2] U.S. Pat. No. 6,673,737
[Patent Literature 3] Japanese Unexamined Patent Application Publication No. 2008-266297
[Patent Literature 4] Japanese Unexamined Patent Application Publication (Translation of PCT Application) No. 2007-501815
[Patent Literature 5] U.S. Patent Publication No. 2014/0005415

Non-Patent Document

[Non Patent Document 1] J. Castells et al., J. Org. Chem., 53, pp 4433-4436(1988)
[Non Patent Document 2] Storey et al., Tetrahedron Letters 46, pp. 7337-7339(2005)
[Non Patent Document 3] Castells et al., Israel Journal of Chemistry Vol. 17 pp. 278-283 (1978)

SUMMARY OF THE INVENTION

In this situation, the present inventors have made extensive and intensive studies toward solving the aforementioned problems. As a result, they have found that a specific supported catalyst for aldehyde coupling reaction (such as benzoin condensation) not only enables the synthesis of an acyloin in high yield while maintaining high activity for a long time but also exhibits excellent recyclability. The specific supported catalyst comprises a carrier having supported thereon a catalyst comprising at least one azolium compound selected from the group consisting of a thiazolium salt, an imidazolium salt, a benzimidazolium salt and a triazolium salt, the azolium compound having, at a nitrogen atom thereof, a substituent selected from the group consisting of an aliphatic group and an aromatic group, each having 6 or more carbon atoms. The present invention has been completed based on this finding.

Specifically, the present invention relates to the following.
(1) A supported catalyst for aldehyde coupling reaction, comprising a carrier having supported thereon a catalyst comprising at least one azolium compound selected from the group consisting of a thiazolium salt, an imidazolium salt, a benzimidazolium salt and a triazolium salt, the azolium compound having, at a nitrogen atom thereof, a substituent selected from the group consisting of an aliphatic group and an aromatic group, each having 6 or more carbon atoms.
(2) The catalyst according to (1), wherein the carrier is an inorganic carrier.
(3) The catalyst according to (1), wherein the carrier is an organic carrier.
(4) The supported catalyst according to (2), wherein the inorganic carrier comprises at least one substance selected from the group consisting of silica, alumina, titania, zirconia, silica-alumina, silica-titania, silica-zirconia and clay.
(5) The supported catalyst according to (2), wherein the inorganic carrier is silica.
(6) The supported catalyst according to (2), wherein the inorganic carrier is clay.
(7) The catalyst according to (3), wherein the organic carrier is at least one polymer carrier selected from the group consisting of styrene polymers, polyolefins, poly(halogenated olefins), nitrile polymers, and (meth)acrylate polymers.
(8) The catalyst according to (3), wherein the organic carrier is a crosslinked polystyrene.
(9) The catalyst according to (1), wherein the azolium compound is a benzimidazolium salt.
(10) A supported catalyst for aldehyde coupling reaction, comprising a carrier having supported thereon a catalyst comprising a benzimidazolium salt.
(11) A method for performing a coupling reaction between aldehyde molecules, comprising reacting aldehyde molecules in the presence of the catalyst according to (I) and a base, the aldehyde molecules each independently represented by the following formula (I):

$$R-CHO \tag{I}$$

wherein R represents a monovalent aliphatic group, a monovalent aromatic group or a monovalent heterocyclic aromatic group.

(12) The method according to (11), wherein the monovalent aromatic group is an unsubstituted or substituted phenyl group and the monovalent heterocyclic aromatic group is an unsubstituted or substituted furyl group.
(13) The method according to (11), wherein the base is selected from the group consisting of tertiary amines, alkoxides, metal hydroxides, metal hydrides, carbonate salts, phosphate salts and cyclic amidines.
(14) The method according to (11), wherein the base is selected from the group consisting of potassium tert-butoxide, 1,8 diazabicyclo[5.4.0]undec-7-ene, and sodium hydride.
(15) A method for regenerating the supported catalyst of (1), comprising treating the supported catalyst used for aldehyde coupling reaction with an acid.
(16) A method for performing a coupling reaction between aldehyde molecules, comprising reacting aldehyde molecules in the presence of the catalyst according to (10) and a base, the aldehyde molecules each independently represented by the following formula (I):

R—CHO  (I)

wherein R represents a monovalent aliphatic group, a monovalent aromatic group or a monovalent heterocyclic aromatic group.
(17) The method according to (16), wherein the monovalent aromatic group is an unsubstituted or substituted phenyl group and the monovalent heterocyclic aromatic group is an unsubstituted or substituted furyl group.
(18) The method according to (16), wherein the base is selected from the group consisting of tertiary amines, alkoxides, metal hydroxides, metal hydrides, carbonate salts, phosphate salts and cyclic amidines.
(19) The method according to (16), wherein the base is selected from the group consisting of potassium tert-butoxide, 1,8 diazabicyclo[5.4.0]undec-7-ene, and sodium hydride.
(20) A method for regenerating the supported catalyst of (10), comprising treating the supported catalyst used for aldehyde coupling reaction with an acid.

DETAILED DESCRIPTION OF THE INVENTION (Supported Catalyst 1 for Aldehyde Coupling Reaction)
The supported catalyst for aldehyde coupling reaction according to the present invention comprises a carrier having supported thereon a catalyst comprising at least one azolium compound selected from the group consisting of a thiazolium salt, an imidazolium salt, a benzimidazolium salt and a triazolium salt, the azolium compound having, at a nitrogen atom thereof, a substituent selected from the group consisting of an aliphatic group and an aromatic group, each having 6 or more carbon atoms (hereinafter, this catalyst is also referred to as "supported catalyst 1"). The aldehyde coupling reaction is a coupling reaction between two aldehyde molecules as described below in more detail, and hence is also referred to simply as "coupling reaction" or the like in the present specification. A coupling reaction between two aromatic aldehydes (such as benzaldehyde) is generally called a "benzoin condensation". The aldehyde coupling reaction in the present invention, however, is not limited to this benzoin condensation as described below in more detail.
As the aforementioned thiazolium salt, there can be mentioned a compound represented by the following formula (1):

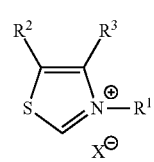

wherein $R^1$ represents an aliphatic group having at least 6 carbon atoms or an aromatic group having at least 6 carbon atoms, each of $R^2$ and $R^3$ independently represents a hydrogen atom, an aliphatic group having 1 or more carbon atoms, or an aromatic group having 6 or more carbon atoms, and X represents a halogen atom.
In the formula (1), the substituent $R^1$ is a substituent bonded to a nitrogen atom contained as a hetero atom in the compound represented by the formula (1). It is presumed that the presence of the substituent $R^1$ enables the catalyst of the present invention to produce an acyloin at high yield while maintaining high activity for a long time, and to exhibit excellent recyclability. With respect to the aliphatic group as the substituent $R^1$, the aliphatic group preferably has 6 to 24 carbon atoms, more preferably 8 to 22 carbon atoms, still more preferably 8 to 20 carbon atoms. With respect to the aromatic group as the substituent $R^1$, the aromatic group preferably has 6 to 24 carbon atoms, more preferably 8 to 22 carbon atoms, still more preferably 8 to 20 carbon atoms.
Specific examples of the aliphatic group as the substituent $R^1$ include linear, branched or cyclic alkyl groups, such as a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a docosyl group, a tricosyl group, a tetracosyl group, a 2-heptylundecyl group, an isostearyl group, a 12-methyl heptadecyl group, a 2-octyl dodecyl group, a 3,7-dimethyl-octyl group, a 3,7-dimethyloctane-3-yl group, a 2-hexyldecyl, a 3,7,11-trimethyldodecyl group, a 1,1,3,3-tetramethylbutyl group, a 3,7,11,15-tetramethylhexadecyl group, a 3,5,5-trimethylhexyl group, a 2,3,4-trimethylpentane-3-yl group, a 2,3,4,6,6-pentamethylheptane-3-yl group, a cyclooctyl group, a cyclodecyl group, a norbornyl group, an adamantyl group, a cyclopentylmethyl group, a cyclopentylethyl group, a cyclopentylpropyl, a cyclopentylbutyl, a cyclohexylmethyl group, a cyclohexylethyl group, a cyclohexylpropyl group, a cyclohexylbutyl group, a cyclooctylmethyl group, a cyclooctylethyl group, a cyclooctylpropyl group and a cyclooctylbutyl group. Of these, an octyl group, a nonyl group, a decyl group, an undecyl group, a dodecyl group, a tridecyl group, a tetradecyl group, a pentadecyl group, a hexadecyl group, a heptadecyl group and an octadecyl group are preferred, and an octyl group, a decyl group, a dodecyl group, a tetradecyl group, a hexadecyl group, and an octadecyl group are more preferred.
Specific examples of the aromatic group as the substituent $R^1$ include aryl groups such as a phenyl group, a naphthyl group, an indenyl group, an anthracenyl group, a biphenyl group and a phenanthryl group; arylalkyl groups such as a benzyl group, a phenethyl group, a diphenylmethyl group, a triphenylmethyl group, a 1-naphthylmethyl group, a 2-naphthylmethyl group, a 2,2-diphenylethyl group, a 3-phenylpropyl group, a 4-phenylbutyl group, and a 5-phenylpentyl group; and alkylaryl groups such as an o-tolyl group, a m-tolyl group, a p-tolyl group, a 2,3-xylyl group, a 2,4-xylyl group, a 2,5-xylyl group, an o-cumenyl group, a m-cumenyl group, a p-cumenyl group, and a mesityl group. Of these, a phenyl group and a benzyl group are preferred.

The aforementioned aliphatic groups and aromatic groups as the substituent $R^1$ may further have a substituent. Examples of the substituent include unsubstituted or substituted alkyl groups such as a methyl group, an ethyl group, a propyl group, an isopropyl group, a butyl group, an isobutyl group, a sec-butyl group, a tert-butyl group, a pentyl group, a hexyl group, a cyclopentyl group, a fluoromethyl group, a trifluoromethyl group, a methoxymethyl group, an ethoxymethyl group, and a methoxyethyl group; unsubstituted or substituted alkoxy groups such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, and a methoxyethoxy group; and halogen atoms such as a fluorine atom and a chlorine atom.

In the formula (1), each of $R^2$ and $R^3$ independently represents a hydrogen atom, an aliphatic group having 1 or more carbon atoms, or an aromatic group having 6 or more carbon atoms. With respect to the aliphatic group as the substituent $R^2$ or $R^3$, the aliphatic group preferably has 1 to 12 carbon atoms, more preferably 1 to 10 carbon atoms, still more preferably 1 to 8 carbon atoms. With respect to the aromatic group as the substituent $R^2$ or $R^3$, the aromatic group preferably has 6 to 12 carbon atoms, more preferably 6 to 11 carbon atoms, still more preferably 6 to 10 carbon atoms. Specific examples of the aliphatic group as the substituent $R^2$ or $R^3$ which has 6 or more carbon atoms include those mentioned above for the substituent $R^1$. Specific examples of the aliphatic group as the substituent $R^2$ or $R^3$ which has less than 6 carbon atoms include chain-like alkyl groups such as a methyl group, an ethyl group, a propyl group, a butyl group and a pentyl group; and cycloalkyl groups such as a cyclopentyl group. Specific examples of the aromatic group as the substituent $R^2$ or $R^3$ include those mentioned above for the substituent $R^1$. Each of the substituents exemplified above as $R^2$ or $R^3$ may further has a substituent, the examples of which include those mentioned above as substituents which the substituent $R^1$ may further has.

In the formula (1), $X^-$ represents a monovalent anion, the examples of which include halide ions such as a chloride ion, a bromide ion, and an iodide ion; borate ions such as a tetrafluoroborate anion; phosphate ions such as hexafluorophosphate anion; antimony acid ions such as hexafluoroantimonate anion; sulfonic acid ions such as a trifluoromethanesulfonic acid anion; and amide ions such as a bis(trifluoromethylsulfonyl) amide anion. Of these, a chloride ion and a bromide ion are preferable.

As the aforementioned imidazolium salt, there can be mentioned a compound represented by the following formula (2):

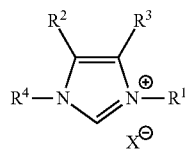

(2)

wherein $R^1$, $R^2$, $R^3$ and X are as defined for the formula (1); and $R^4$ represents a hydrogen atom, an aliphatic group having 1 or more carbon atoms, or an aromatic group having 6 or more carbon atoms.

In the formula (2), the aliphatic group as the substituent $R^4$ preferably has 1 to 24 carbon atoms, more preferably 1 to 22 carbon atoms, still more preferably 1 to 20 carbon atoms. The aromatic group as the substituent $R^4$ preferably has 6 to 24 carbon atoms, more preferably 6 to 22 carbon atoms, still more preferably 6 to 20 carbon atoms.

With respect to $R^1$, $R^2$, $R^3$ and X in the formula (2), specific examples thereof include those respectively mentioned above for the formula (1). Further, specific examples of $R^4$ in the formula (2) include those mentioned above for $R^1$, $R^2$ and $R^3$ in the formula (1). With respect to the aliphatic group as $R^4$ used when the carrier is a clay which is described below, it is especially preferred to use an aliphatic group having 6 or more carbon atoms as in the case of $R^1$ for enhancing the effects of the present invention.

As the aforementioned benzimidazolium salt, there can be mentioned a compound represented by the following formula (3):

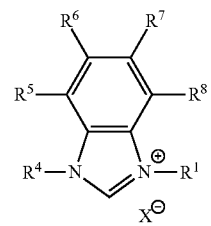

(3)

wherein $R^1$ and X are as defined for the formula (1); $R^4$ is as defined for the formula (2); and each of $R^5$, $R^6$, $R^7$ and $R^8$ has the same meaning as defined for $R^2$ and $R^3$ in the formula (1).

With respect to $R^1$ and X in the formula (3), specific examples thereof include those respectively mentioned above for the formula (I). Specific examples of $R^4$ in the formula (3) include those mentioned above for $R^1$, $R^2$ and $R^3$ in the formula (1). Further, specific examples of $R^5$, $R^6$, $R^7$ and $R^8$ in the formula (3) include those mentioned above for $R^2$ and $R^3$ in the formula (1).

As the aforementioned triazolium salt, there can be mentioned a compound represented by the following formula (4):

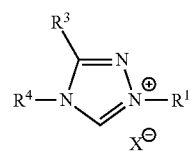

(4)

wherein $R^1$, $R^3$ and X are as defined for the formula (1); and $R^4$ is as defined for the formula (2).

With respect to $R^1$, $R^3$ and X in the formula (4), specific examples thereof include those respectively mentioned above for the formula (I). Specific examples of $R^4$ in the formula (4) include those mentioned above for $R^1$, $R^2$ and $R^3$ in the formula (1).

Of the compounds of the formulae (1) to (4), each of which is usable as the azolium compound in the present invention, the benzimidazolium salt of the formula (3) is preferred from the viewpoint of the catalytic activity, the recyclability, and the readiness of preparation.

All of the above-mentioned azolium compounds can be produced by applying the known methods with appropriate modifications. That is, any of the above-mentioned azolium compounds can be produced by, for example, a method in which an azole compound (thiazole, imidazole, benzimidazole or triazole) which is either obtainable by any conventional process or commercially available is reacted with an organohalogen compound.

For example, the thiazolium salt of the formula (1) can be produced by application of a method described in Chem. Commun., 47, 573-575(2011), J. Amer. Chem. Soc., 130, 2234-2245(2008), International Patent Application Publication No. 2014/133115 or the like, where appropriate raw materials are selected in view of the intended substituents (such as $R^1$ in the formula (1)) and the intended anion ($X^-$ in the formula (1)). The imidazolium salt of the formula (2) can be produced by application of a method described in Starikova, O. V.; Dolgushin, G. V. Larina, L. I.; Komarova, T. N.; Lopyrev. V. A. ARKIVOC (Gainesville Fla., United States) (2003), (13), 119-124, Japanese Patent Application Unexamined Publication No. 2008-133248 or the like, where appropriate raw materials are selected in view of the intended substituents (such as $R^1$ in the formula (2)) and the intended anion ($X^-$ in the formula (2)). The benzimidazolium salt of the formula (3) can also be produced by application of a method described in the aforementioned Lopyrev, V. A. ARKIVOC (Gainesville Fla., United States) (2003), (13), 119-124 or the like, where appropriate raw materials are selected in view of the intended substituents (such as $R^1$ in the formula (3)) and the intended anion ($X^-$ in the formula (3)). The triazolium salt of the formula (4) can be produced by application of a method described in Japanese Patent Unexamined Publication No. Hei 6-211723 or the like, where appropriate raw materials are selected in view of the intended substituents (such as $R^1$ in the formula (4)) and the intended anion ($X^-$ in the formula (4)).

The aforementioned carrier may either be an inorganic carrier or an organic carrier. As the inorganic carrier, it is preferred to use a carrier comprising at least one substance selected from the group consisting of silica, alumina, titania, zirconia, silica-alumina, silica-titania, silica-zirconia and clay, and it is more preferred that the inorganic carrier is silica or clay. Specific examples of the clay include kaolinite, montmorillonite and attapulgite, of which montmorillonite is preferred. When a clay is used as the carrier, the clay forms an ionic bond with the azolium compound; therefore, it is possible to have the azolium compound supported on the clay even without using the halogen-substituted alkoxysilane (5) described below.

As the organic carrier, it is preferred to use a carrier comprising at least one polymer carrier selected from the group consisting of styrene polymers, polyolefins, poly (halogenated olefins), nitrile polymers and (meth)acrylate polymers, and it is more preferred to use a crosslinked polystyrene. Here, the "crosslinked polystyrene" means a polymer composed mainly of crosslinked copolymer of a monovinyl aromatic compound such as styrene, vinylxylene or vinylnaphthalene with a polyvinyl aromatic compound such as divinylbenzene, divinyltoluene, divinylxylene, divinylnaphthalene, trivinylbenzene, bisvinyldiphenyl or bisbiphenylethane. Such a crosslinked copolymer may further be copolymerized with a methacrylate such as glycerol methacrylate or ethylene glycol dimethacrylate.

The form of the carrier used in the present invention may be any form generally employed in the art, such as spheres (for example, spherical particles), particles, fibers, granules, monolith columns, hollow fibers or a membrane (for example, flat membrane), and is not particularly limited. Of these, the form of spheres, a membrane, particles or fibers is preferred.

The carrier in the form of spheres, fibers, particles or granules generally has an average particle size within a range of from 1 μm to 10 mm, preferably within a range of from 2 μm to 1 mm. Further, the carrier may be porous or non-porous. The average pore size of the porous carrier is usually from 1 nm to 1 μm, preferably within a range of from 1 nm to 300 nm.

The method for immobilizing the aforementioned azolium compound on the carrier is not particularly limited, and any conventional methods can be employed. For example, when the carrier is an inorganic compound having hydroxyl groups on the surface thereof, such as silica, the supported catalyst of the present invention can be produced by a method comprising: reacting the azolium compound with a halogen-substituted alkoxysilane compound represented by the following formula (5) (hereinafter, referred to as "halogen-substituted alkoxysilane (5)); and reacting the resulting product with a carrier.

$$Y\text{—}R^9\text{—}SiR^{10}{}_n\text{—}(OR^{11})_{3-n} \quad\quad (5)$$

wherein each of $R^9$, $R^{10}$ and $R^{11}$ has the same meaning as defined for $R^2$ and $R^3$ in the formula (1), n is 0, 1 or 2, and Y represents a chlorine atom, a bromine atom or a iodine atom.

With respect to the specific method and conditions, for example, reference can be made to the aforementioned Patent Document 3 and the like.

Further, as mentioned above, when a clay is used as the inorganic carrier, the clay can be ionically bonded to the azolium compound; therefore, the supported catalyst of the present invention can be obtained even without using the halogen-substituted alkoxysilane (5). In this case, the aforementioned Patent Document 5 and the like can be referred to for specific information on the method and conditions.

Also in the case where an organic carrier is used, the immobilization of the azolium compound on the carrier can be performed by any of the conventional methods. For example, the azolium compound can be immobilized on a soluble or insoluble (crosslinked) polystyrene. As an example of specific method, there can be mentioned a method in which the azolium compound is reacted with styrene and divinylbenzene as a crosslinking agent in the presence of a radical polymerization initiator such as 2,2'-azobisisobutyronitrile. As a more simple method, when a commercially available chloromethyl polystyrene resin crosslinked with divinylbenzene (the so-called "Merrifield's peptide resin") is used as an organic carrier, a supported catalyst comprising a polystyrene carrier having supported thereon an azolium salt can be obtained by reacting the chloromethyl polystyrene resin with the aforementioned azole compound (i.e., thiazole, imidazole, benzimidazole or triazole).

The amount of the carrier is not particularly limited, but is generally 0.1 to 1,000 parts by weight, relative to 100 parts by weight of the azolium compound, for achieving the purpose of the present invention.

(Supported Catalyst 2 for Aldehyde Coupling Reaction)

According to another aspect of the present invention, there is provided a supported catalyst for aldehyde coupling reaction comprising a carrier having supported thereon a catalyst comprising a benzimidazolium salt (hereinafter, this catalyst is also referred to as "supported catalyst 2 for aldehyde coupling reaction). Here, as the benzimidazolium salt, there can be mentioned a compound represented by the following formula (6):

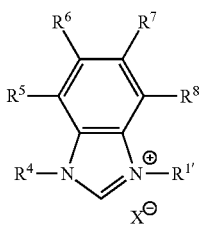
(6)

wherein $R^{1'}$ has the same meaning as defined for $R^2$ and $R^3$ in the formula (1), and $R^4$, $R^5$, $R^6$, $R^7$, $R^8$ and X are as defined for the formula (3).

Specific examples of $R^{1'}$, $R^5$, $R^6$, $R^7$ and $R^8$ in the formula (6) include those mentioned above for $R^2$ and $R^3$ in the formula (1). Specific examples of $R^4$ in the formula (6) include those mentioned above for $R^1$, $R^2$ and $R^3$ in the formula (1). Further, specific examples of X in the formula (6) include those mentioned above for the formula (1).

With respect to the carrier and the method for producing the supported catalyst 2, the same applies as mentioned above for the supported catalyst 1.

The supported catalyst 2 comprising the benzimidazolium salt is advantageous in respect of the catalytic activity, the recyclability and the readiness of preparation, as compared to the other supported catalyst comprising an azolium compound.

(Method for Performing Aldehyde Coupling Reaction)

According to still another aspect of the present invention, there is provided a method for performing a coupling reaction between aldehyde molecules, comprising reacting aldehyde molecules in the presence of the supported catalyst 1 or 2 for aldehyde coupling reaction and a base, the aldehyde molecules each independently represented by the following formula (I):

R—CHO    (I)

wherein R represents a monovalent aliphatic group, a monovalent aromatic group or a monovalent heterocyclic aromatic group.

Here, the aldehyde is not particularly limited as long as it is a compound having at least one formyl group within a molecule thereof. The coupling reaction in the present invention includes a homocoupling reaction between molecules of the same aldehyde compound, and a cross coupling reaction between different aldehyde compounds. Examples of the homocoupling reaction include a reaction where two molecules of an aldehyde compound represented by the formula (a) (hereinafter, referred to as "aldehyde (a)"):

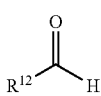
(a)

(wherein $R^{12}$ represents a hydrogen atom, a substituted or unsubstituted aliphatic group, a substituted or unsubstituted aromatic group or a substituted or unsubstituted heteroaromatic group) are coupled together to form an acyloin (α-hydroxyketone) represented by the following formula (b) (hereinafter, referred to as "acyloin (b)"):

(b)

(wherein $R^{12}$ is as defined for the formula (a)) (hereinafter, this reaction is referred to as "coupling reaction (I)").

Examples of the cross coupling reaction include a reaction where the aldehyde (a) and an aldehyde compound represented by the formula (c) (hereinafter, referred to as "aldehyde (c)"):

(c)

(wherein $R^{13}$ represents a hydrogen atom, a substituted or unsubstituted aliphatic group, a substituted or unsubstituted aromatic group or a substituted or unsubstituted heteroaromatic group, with the proviso that $R^{13}$ is different from $R^{12}$) are coupled together to form an acyloin (α-hydroxyketone) represented by the following formula (d) (hereinafter, referred to as "acyloin (b)"):

(d)

(wherein $R^{12}$ and $R^{13}$ are as defined above) (hereinafter, this reaction is referred to as "coupling reaction (II)").

In the present specification, the coupling reaction (I) and the coupling reaction (II) are also collectively referred to as "the present coupling reaction".

Hereinbelow, explanations are made with respect to the coupling reactions (I) and (II).

Examples of the aliphatic groups as $R^{12}$ and $R^{13}$ in the formulae (a) and (c) include a linear, branched or cyclic alkyl group having 1 to 20 carbon atoms such as a methyl group, an ethyl group, a n-propyl group, an isopropyl group, a n-butyl group, an isobutyl group, a sec-butyl group, a tert-butyl group, a n-pentyl group, a n-decyl group, a cyclopropyl group, a 2,2-dimethylcyclopropyl group, a cyclopentyl group, a cyclohexyl group and a menthyl group. Examples of the substituent of the aforementioned alkyl groups include unsubstituted or substituted alkoxy groups such as a methoxy group, an ethoxy group, a propoxy group, an isopropoxy group, a butoxy group, an isobutoxy group, a sec-butoxy group, a tert-butoxy group, a trifluoromethoxy group, a benzyloxy group, a 4-methylbenzyloxy group, a 4-methoxybenzyloxy group, and a 3-phenoxybenzyloxy group; unsubstituted or substituted aryloxy groups such as a phenoxy group, a 2-methylphenoxy group, a 4-methylphenoxy group, a 4-methoxyphenoxy group, and a 3-phenoxyphenoxy group; unsubstituted or substituted alkylcarbonyl groups such as an acetyl group, a propionyl group, a benzylcarbonyl group, a 4-methylbenzylcarbonyl group, and a 4-methoxybenzylcarbonyl group; unsubstituted or substituted arylcarbonyl groups such as a benzoyl group, a 2-methylbenzoyl group, a 4-methylbenzoyl group, and a 4-methoxybenzoyl group; unsubstituted or substituted alkylthio groups such as a methylthio group, an ethylthio group, and an isopropylthio group; and halogen atoms such as a fluorine atom, a chlorine atom, and a bromine atom. Examples of the substituted alkyl group include a chloromethyl group, a fluoromethyl group, a trifluoromethyl group, a methoxymethyl group, an ethoxymethyl group, a methoxyethyl group, a methoxycarbonylmethyl group, and a 1-ethoxycarbonyl-2,2-dimethyl-3-cyclopropyl group.

Examples of the aromatic groups as $R^{12}$ and $R^{13}$ in the formulae (a) and (c) include aryl groups having 6 to 20 carbon atoms such as a phenyl group and a naphthyl group. Examples of the substituent of the aforementioned aryl groups include unsubstituted or substituted alkyl groups such as a methyl group, an ethyl group, a propyl group, an isopropyl group, a butyl group, an isobutyl group, a sec-butyl group, a tert-butyl group, a pentyl group, a hexyl group, a cyclopentyl group, a fluoromethyl group, a trifluoromethyl group, a methoxymethyl group, an ethoxymethyl group, and a methoxyethyl group; unsubstituted or substituted alkoxy groups such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, and a methoxyethoxy group; unsubstituted or substituted aryloxy groups such as a phenoxy group, a 2-methylphenoxy group, a 4-methylphenoxy group, a 4-methoxyphenoxy group, and a 3-phenoxyphenoxy group; unsubstituted or substituted alkylcarbonyl groups such as an acetyl group, a propionyl group, a benzylcarbonyl group, a 4-methylbenzylcarbonyl group, and a 4-methoxybenzylcarbonyl group; and halogen atoms such as a fluorine atom and a chlorine atom. Examples of the substituted aryl group include a 2-methylphenyl group, a 4-chlorophenyl group, a 4-methylphenyl group, a 4-methoxyphenyl group, and a 3-phenoxyphenyl group.

Examples of the heteroaromatic groups as $R^{12}$ and $R^{13}$ include heteroaryl groups having 4 to 20 carbon atoms which contain at least one heteroatom such as a nitrogen atom, an oxygen atom and a sulfur atom, for example, a pyridyl group and a furyl group. Examples of the substituent of the aforementioned heteroaryl groups include unsubstituted or substituted alkyl groups such as a methyl group, an ethyl group, a propyl group, an isopropyl group, a butyl group, an isobutyl group, a sec-butyl group, a tert-butyl group, a pentyl group, a hexyl group, a cyclopentyl group, a fluoromethyl group, a trifluoromethyl group, a methoxymethyl group, an ethoxymethyl group, and a methoxyethyl group; unsubstituted or substituted alkoxy groups such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, and a methoxyethoxy group; unsubstituted or substituted aryloxy groups such as a phenoxy group, a 2-methylphenoxy group, a 4-methylphenoxy group, a 4-methoxyphenoxy group, and a 3-phenoxyphenoxy group; unsubstituted or substituted alkylcarbonyl groups such as an acetyl group, a propionyl group, a benzylcarbonyl group, a 4-methylbenzylcarbonyl group, and a 4-methoxybenzylcarbonyl group; and halogen atoms such as a fluorine atom and a chlorine atom. Examples of the substituted heteroaryl group include a 2-chloropyridyl group and a 5-methylfurfuryl group.

Examples of the aldehydes (a) and (c) include aliphatic aldehydes such as formaldehyde, cyclopentanecarboaldehyde, cyclohexanecarboaldehyde, 2-methylpropanal, 2,2-dimethylpropanal, 3-methylthiopropanal, 2,2-dimethylbutanal, 1-methylcyclohexanecarboaldehyde, 2,2-dimethylnonanal, and methyl 2,2-dimethyl-3-oxopropanoate; aromatic aldehydes such as benzaldehyde, 4-fluorobenzaldehyde, 4-nitrobenzaldehyde, 3-bromobenzaldehyde, 2-chlorobenzaldehyde, 4-methylbenzaldehyde, 3-methoxybenzaldehyde, 3,4,5-trimethoxybenzaldehyde, 3,4-methylenedioxybenzaldehyde, and 1-naphthaldehyde; and heteroaromatic aldehydes such as furfural, hydroxymethyl furfural, 2-pyridine carbaldehyde, and 3-pyridine carbaldehyde. Of these, aromatic aldehydes and heteroaromatic aldehydes are preferred as the aldehydes used for the coupling reactions (I) and (II). Especially preferred are aromatic aldehydes (such as benzaldehyde) in which the aromatic group is an unsubstituted or substituted phenyl group, and heteroaryl aldehydes (such as furfural and hydroxymethyl furfural) in which the heterocyclic aromatic group is an unsubstituted or substituted furyl group. Each of the aldehydes (a) and (c) may either be one which is commercially available or one which is produced by any of the conventional methods.

Each of the coupling reactions (I) and (II) is preferably performed in the presence of a base. The base may be organic or inorganic, and is preferably selected from the group consisting of tertiary amines, alkoxides, metal hydroxides, metal hydrides, carbonate salts, phosphate salts and cyclic amidines. Examples of tertiary amines include triethylamine, trioctylamine, and diisopropylethylamine. Examples of alkoxides include sodium methoxide, sodium ethoxide, and potassium tert-butoxide. Examples of metal hydroxides include alkali metal hydroxides such as sodium hydroxide and potassium hydroxide; and alkaline earth metal hydroxides such as magnesium hydroxide and calcium hydroxide. Examples of metal hydrides include sodium hydride and potassium hydride. Examples of carbonate salts include alkali metal carbonates such as sodium carbonate and potassium carbonate; and alkaline earth metal carbonates such as magnesium carbonates and calcium carbonate. Examples of phosphate salts include sodium phosphate, potassium phosphate and a calcium phosphate. Examples of cyclic amidines include diazabicycloundecene (DBU, 1,8-diazabicyclo [5.4.0] undec-7-ene) and diazabicyclononene (DBN, 1,5-diazabicyclo [4.3.0]-5-nonene).

The amount of the base is generally 0.3 to 2 mol per mol of the azolium cation in the supported catalyst.

Each of the coupling reactions (I) and (II) is generally performed in a solvent. Examples of the solvent include aromatic hydrocarbon solvents such as toluene, xylene, and chlorobenzene; aliphatic hydrocarbon solvents such as pentane, hexane, and heptane; halogenated hydrocarbon solvents such as dichloromethane, dichloroethane, and chloroform; ether solvents such as diethyl ether, methyl tert-butyl ether, and tetrahydrofuran (THF); ester solvents such as ethyl acetate; amide solvents such as N,N-dimethylformamide, and N,N-dimethylacetamide; alcohol solvents such as methanol, and ethanol; and water. The amount of the solvent used is not particularly limited; however, from a practical point of view, the amount is generally 100 parts by weight or less relative to 1 part by weight of the supported catalyst in view of volume efficiency.

In the case of the coupling reaction (I), the supported catalyst used is generally used in an amount such that the amount of azolium cation is from 0.005 to 0.5 mol, and preferably from 0.01 to 0.3 mol per mol of the aldehyde (a). In the case of the coupling reaction (11), the supported catalyst used is generally used in an amount such that the amount of azolium cation is from 0.005 to 0.5 mol, and preferably from 0.01 to 0.3 mol per mol of the total of the aldehydes (a) and (c).

In the case of the coupling reaction (II), the aldehydes (a) and (c) may be used in equimolar amounts, or one of the aldehydes (a) and (c) may be used in a larger amount. It is preferred that the aldehyde (c) is used in an amount of 0.7 to 1.5 mol per mol of the aldehyde (a).

In general, the reaction temperature is in the range of from −20 to 200° C.

Each of the coupling reactions (I) and (II) is performed by mixing the aldehyde (a) (and the aldehyde (c)) with the supported catalyst, if necessary, in the presence of a solvent and a base, where the order of mixing is not particularly limited. It is preferred that the reaction is performed in a manner such that a base is added to a mixture of a solvent, the aldehyde (a) (and the aldehyde (c)) and the supported catalyst under temperature condition for the reaction.

Each of the coupling reactions (I) and (II) may be performed under normal pressure condition or under pressurized condition. The progress of the reaction can be monitored by conventional analysis such as gas chromatography, high performance liquid chromatography, thin layer chromatography, NMR, IR or the like.

After completion of the reaction, the acyloin (b) or acyloin (d) can be isolated by a method wherein the obtained reaction mixture is subjected to a solid-liquid separation treatment such as filtration and decantation, to remove the supported catalyst, followed by a general isolation treatment such as crystallization, liquid separation or concentration. The isolated acyloin (b) or acyloin (d) may be further purified by a conventional purification treatment such as distillation or column chromatography.

Examples of the thus obtained acyloin (b) include 2-hydroxy-1,2-diphenylethanone (benzoin), 2-hydroxy-1,2-di(2-furyl)ethanone (furoin), 5,5'-di(hydroxymethyl)furoin, 2-hydroxy-1,2-di(4-chlorophenyl)ethanone, 2-hydroxy-1,2-dicyclohexylethanone, 2-hydroxy-1,2-di(3-methylphenyl) ethanone, 2-hydroxy-1,2-di(2-fluorophenyl)ethanone, 2-hydroxy-1,2-di(3-methoxyphenyl)ethanone, 2-hydroxy-1,2-di (3,4-methylenedioxyphenyl)ethanone, 2-hydroxy-1,2 dinaphthylethanone, and 2-hydroxy-1,2-di(3-pyridyl)ethanone. Examples of the acyloin (d) include 2-hydroxy-1-(4-methoxyphenyl)-2-phenylethanone, 2-hydroxy-1-(4-chlorophenyl)-2-phenylethanone, 2-hydroxy-1-(2-fluorophenyl)-2-phenylethanone, 4-(methylthio)-2-oxo-1-butanol, 1-hydroxy-2-propanone, 1-hydroxy-2-butanone, 1-hydroxy-2-pentanone, and 2-hydroxy-1-cyclohexanone.

When the supported catalyst is recovered from the reaction system of the present coupling reaction by the solid-liquid separation treatment, the recovered catalyst as such can be recycled as the catalyst for the present coupling reaction, or can be recycled if necessary after washing and treatment such as the regeneration treatment described below.

In still another aspect of the present invention, there is provided a method for regenerating the supported catalyst 1 or 2, comprising treating the supported catalyst used for aldehyde coupling reaction with an acid. The acid usable in this method is not particularly limited, but it is preferred to use an acid which can quench the aldehyde coupling reaction. In this case, by adding an acid capable of quenching the reaction, the carbene in situ formed in the reaction by the action of base can be converted back into the azolium salt by reacting with the acid, while simultaneously quenching the reaction. Examples of the acid include hydrogen chloride, acetic acid, maleic acid, sulfuric acid and sulfonic acid. Each of these acids is generally used in the form of an aqueous solution. The preferred concentration of acid in an aqueous solution varies depending on the type of acid etc., but is preferably 0.01 to 50% by weight.

As a method for repeatedly performing an aldehyde coupling reaction by regenerating the supported catalyst 1 or 2 which has been used, there can be mentioned a method comprising adding an aqueous solution of the above-mentioned acid to the reaction system for aldehyde coupling reaction to quench the reaction, separating the catalyst from the reaction system by filtration, washing the catalyst several times (preferably 1 to 5) times, drying the catalyst at room temperature to 200° C. for 0.1 to 50 hours, and performing an aldehyde coupling reaction in the presence of the catalyst.

EXAMPLES

Hereinbelow, the present invention is described in more detail with reference to the Examples which, however, should not be construed as limiting the scope of the present invention.

In the following Examples and Comparative Examples, the measurements by $^1$H-NMR and $^{13}$C-NMR are performed by Varian Inova 400 MHz spectrometer.

Example 1

(Production of Benzimidazolium Salt BI(1))

A 250 mL three-necked round-bottom flask equipped with a stir bar and a condenser was charged with benzimidazole (5.00 g, 42.3 mmol), oil free sodium hydride (NaH) (1.02 g, 42.3 mmol), and dry tetrahydrofuran (THF) (30 mL) at 0° C. The resulting mixture was stirred for 30 minutes under nitrogen atmosphere. Then, (3-chloropropyl)triethoxysilane (10.2 g, 42.3 mmol) was added, and the reaction mixture was stirred under reflux for 24 hours. The reaction mixture was cooled to room temperature, filtered and washed with dry dichloromethane. The filtrate was concentrated in vacuo, and colorless oil was obtained which was used as such without any further purification. To the resulting product was added dry acetonitrile (30 mL) and dodecyl bromide (15.8 g, 63.5 mmol). The resulting mixture was stirred under reflux for 48 hours under nitrogen atmosphere. The mixture was then evaporated to dryness in vacuo. The resulting residue was washed with dry n-pentane and 1-(3-(triethoxysilylpropyl)-3-dodecyl benzimidazolium bromide BI(1) was isolated as a white solid (22.1 g, yield: 91%).

$^1$H NMR (400 MHz, CDCl$_3$): δ 0.72 (t, 2H, SiCH$_2$), 0.85 (t, 3H, CH$_2$CH$_2$CH$_3$), 1.10-1.50 (m, 27H, NCH$_2$CH$_2$(CH$_2$)$_9$CH$_3$ and Si(OCH$_2$CH$_3$)$_3$), 2.09 (m, 4H, NCH$_2$CH$_2$), 3.81 (q. J=7.2 Hz, 6H, Si(OCH$_2$CH$_3$)$_3$), 4.64 (m, 4H, NCH$_2$), 7.68 (m, 4H, Ar—H), 11.49 (s, 1H, NCHN). $^{13}$C NMR (100 MHz, CDCl$_3$): δ 7.10, 13.95, 18.16, 22.50, 23.44, 26.42, 28.91, 29.14, 29.21, 29.23, 29.34, 29.41, 31.72, 47.58, 49.15, 58.47, 113.11, 127.04, 131.17, 142.30 ppm. HRMS calculated for C$_{28}$H$_{51}$O$_3$SiN$_2^+$[M]$^+$: m/z=491.3669. found: 491.3663.

(Production of Supported Catalyst for Aldehyde Coupling Reaction)

Silica with a particle size of 10 to 14 μm (8.0 g, dried at 120° C. under vacuum overnight prior to use) and the obtained benzimidazolium salt BI(1) (13.7 g, 24 mmol) were co-dispersed in anhydrous toluene (60 mL) in a 250 mL three-neck round bottom flask. The resulting mixture was stirred under reflux for 24 hours under nitrogen atmosphere. From the mixture was filtered a supported catalyst (Silica-g-BI(1)) composed of silica having supported thereon the benzimidazolium salt BI(1), which was then washed with dichloromethane, and dried at 70° C. under vacuum overnight. With respect to the obtained supported catalyst Silica-g-BI(1) and the silica alone, a thermogravimetric analysis (TGA) was conducted with a heating rate of 10° C./min. from 20 to 900° C. under nitrogen atmosphere. From the obtained TGA curves of the silica and the supported catalyst, the content of benzimidazolium salt BI(1) in the supported catalyst was calculated and found to be 425.6 μmol/g.

(Aldehyde Coupling Reaction)

Furfural (0.166 mL, 2 mmol), THF (3 mL), the supported catalyst Silica-g-BI(1) (0.47 g, BI1: 0.2 mmol) and 1,8-diazabicyclo [5.4.0] undec-7-ene (DBU, 30 μL, 0.2 mmol) were loaded into a 20 mL vial in the glovebox. The reaction mixture was stirred under a nitrogen atmosphere at room temperature in the glovebox for 6 hours. After the reaction, 37% HCl (18 μL, 0.214 mmol) was added in the vial to quench the reaction. The in situ formed carbene was converted back into the benzimidazolium salt by reacting with HCl. Then, the solid catalyst was filtered, washed several times with methanol, and dried at 70° C. under vacuum overnight. The recovered catalyst was reloaded into the 20 mL vial to catalyze the furfural coupling reaction under the same conditions as mentioned above. The reaction products were analyzed by $^1$H-NMR, and the furoin yields were obtained from the $^1$H-NMR spectra. The conditions and results are shown in Table 1.

Examples 2 to 5

The same procedure was repeated as in Example 1 to perform aldehyde coupling reactions except that the type and amount of base were changed as shown in Table 1. The conditions and results are shown in Table 1.

TABLE 1

| | Cycle of reaction | Catalyst | Catalyst loading (mol %) | Base (mol %) | Solvent | Quenching agent | Acyloin yield (%) | Average yield (%) |
|---|---|---|---|---|---|---|---|---|
| Example 1 | 1 | Silica-g-BI(1) | 10 | DBU/10 | THF | HCl | 96.6 | 96.3 |
| | 2 | Recycled | — | DBU/10 | THF | HCl | 96.6 | |
| | 3 | " | — | DBU/10 | THF | HCl | 96.4 | |
| | 4 | " | — | DBU/10 | THF | HCl | 96.5 | |
| | 5 | " | — | DBU/10 | THF | HCl | 96.5 | |
| | 6 | " | — | DBU/10 | THF | HCl | 96.5 | |
| | 7 | " | — | DBU/10 | THF | HCl | 95.7 | |
| | 8 | " | — | DBU/10 | THF | HCl | 95.5 | |
| | 9 | " | — | DBU/10 | THF | HCl | 96.3 | |
| | 10 | " | — | DBU/10 | THF | HCl | 96.3 | |
| Example 2 | 1 | Silica-g-BI(1) | 10 | DBU/20 | THF | HCl | 96.6 | 96.4 |
| | 2 | Recycled | — | DBU/20 | THF | HCl | 96.4 | |
| | 3 | " | — | DBU/20 | THF | HCl | 96.0 | |
| | 4 | " | — | DBU/20 | THF | HCl | 95.7 | |
| | 5 | " | — | DBU/20 | THF | HCl | 96.8 | |
| | 6 | " | — | DBU/20 | THF | HCl | 96.5 | |
| | 7 | " | — | DBU/20 | THF | HCl | 95.2 | |
| | 8 | " | — | DBU/20 | THF | HCl | 97.5 | |
| | 9 | " | — | DBU/20 | THF | HCl | 96.4 | |
| | 10 | " | — | DBU/20 | THF | HCl | 97.4 | |
| Example 3 | 1 | Silica-g-BI(1) | 10 | Et$_3$N[1]/10 | THF | HCl | 0.5 | |
| Example 4 | 1 | Siiica-g-BI(1) | 10 | Et$_3$N/20 | THF | HCl | 29.1 | |
| Example 5 | 1 | Silica-g-BI(1) | 10 | KO$^t$Bu[2]/10 | THF | HCl | 96.5 | 96.5 |
| | 2 | Recycled | — | KO$^t$Bu/10 | THF | HCl | 96.5 | |
| | 3 | " | — | KO$^t$Bu/10 | THF | HCl | 96.6 | |
| | 4 | " | — | KO$^t$Bu/10 | THF | HCl | 96.4 | |
| | 5 | " | — | KO$^t$Bu/10 | THF | HCl | 96.5 | |

Note:

[1]Et$_3$N means triethylamine.

[2]KO$^t$Bu means potassium tert-butoxide.

Comparative Examples 1 and 2

The same procedure was repeated as in Example 1 to perform benzoin condensation reactions except that the type and amount of base were changed as shown in Table 2 and the quenching of reaction with HCl was not performed.
The conditions and results are shown in Table 2.

TABLE 2

|  | Cycle of reaction | Catalyst | Catalyst loading (mol %) | Base (mol %) | Solvent | Acyloin yield (%) |
|---|---|---|---|---|---|---|
| Comparative Example 1 | 1 | Silica-g-BI(1) | 10 | NaH/10 | THF | 97.1 |
|  | 2 | Recycled | — | NaH/10 | THF | 82.6 |
|  | 3 | " | — | NaH/10 | THF | 63.1 |
| Comparative Example 2 | 1 | Silica-g-BI(1) | 10 | DBU/10 | THF | 97.5 |
|  | 2 | Recycled | — | DBU/10 | THF | 55.7 |
|  | 3 | " | — | DBU/10 | THF | 28.4 |

As can be seen from Table 1, when DBU (10 mol %) was used as the base (Example 1), the furoin yields for all the ten cycles remained at about 96% (the average yield was 96.3%). That is, there was almost no decrease in the catalytic activity throughout the ten cycles.

Similar results were obtained when 20 mol % of DBU or 10 mol % of KO$^t$Bu was used as the base (Example 5).

On the other hand, as can be seen from Table 2, the furoin yields decreased rapidly in the second and third cycles without quenching with acid (Comparative Example 1 and 2).

These results indicated that the quenching process with HCl was effective for regenerating the catalyst while maintaining the initial activity thereof.

Example 6

Using the catalyst silica-g-BI(1) produced in the same manner as in Example 1, a coupling reaction of hydroxymethyl furfural (HMF) was performed. Specifically, HMF (252.2 mg, 2 mmol), THF (3 mL), silica-g-BI(1) (BI: 0.2 mmol, 10 mol %) and a base (0.4 mmol, 20 mol %) were loaded into a 20 mL vial in the glovebox. The reaction mixture was stirred under a nitrogen atmosphere at room temperature for 24 hours. After the reaction, 37% HCl (36 µL, 0.428 mmol) was added in the vial to quench the reaction. The in situ formed carbene was converted back into BI by reacting with HCl. Then, the recovered solid catalyst was filtered, washed several times with methanol, and dried at 70° C. under vacuum overnight. The recycled catalyst was reloaded into a 20 mL vial to catalyze the HMF self-coupling reaction under the same conditions as mentioned above. The reaction products were analyzed by $^1$H-NMR, and the yields of 5,5'-di(hydroxymethyl)furoin (DHMF) were obtained from the $^1$H-NMR spectra. The conditions and results are summarized in Table 3.

Alternatively, HMF (1.0 g, 7.93 mmol), THF (12 mL), Silica-g-BI(1) (1.864 g, 0.793 mmol, 10 mol %) and DBU (0.242 g, 1.586 mmol, 20 mol %) were loaded into a 50 mL, round-bottom flask in the glovebox. The reaction mixture was stirred under a nitrogen atmosphere at room temperature for 24 hours. The reaction was quenched with 37% HCl (134 µL, 1.595 mmol). Thereafter, the recovered solid catalyst was filtered and washed with methanol. The filtrate was concentrated under reduced pressure, and the product was purified by silica gel column chromatography (hexanes/ethyl acetate/methanol volume ratio=6/4/2). DHMF (0.827 g, 82.7% isolated yield) was obtained as a pale yellow solid after vacuum drying.

$^1$H NMR (400 MHz, DMSO): δ 4.31 (s, 2 H, CH$_2$OH), 4.46 (s, 2 H, CH$_2$OH), 5.19 (br s, 1H, CH$_2$OH), 5.52 (br s, 1H, CH$_2$OH), 5.74 (s, 1H, CHOH), 6.09 (br s, 1H, CHOH), 6.22, 6.34, 6.51, 7.50 (4H, furan ring H).

TABLE 3

|  | Cycle of reaction | Catalyst (mol %) | Base (mol %) | Time (hours) | Quenching reagent | DHMF yield (%) | Average yield (%) |
|---|---|---|---|---|---|---|---|
| Example 6 | 1 | Silica-g-BI(1) | DBU/20 | 24 | HCl | 94.3 | 92.6 |
|  | 2 | Recycled | DBU/20 | 24 | HCl | 94.3 |  |
|  | 3 | " | DBU/20 | 24 | HCl | 93.1 |  |
|  | 4 | " | DBU/20 | 24 | HCl | 91.4 |  |
|  | 5 | " | DBU/20 | 74 | HCl | 89.7 |  |

Example 7

Production of Benzimidazolium Salt BI(2)

To a 250 mL three-necked round-bottom flask equipped with a stir bar and a condenser was transferred benzimidazole (5.00 g, 42.3 mmol), sodium hydrogen carbonate (NaHCO$_3$) (3.56 g, 42.3 mmol), dodecyl bromide (31.63 g, 126.9 mmol), and acetonitrile (30 mL). The resulting mixture was stirred at reflux for 72 hours under nitrogen atmosphere. The reaction mixture was cooled to room temperature, and dichloromethane (50 mL) was added to the mixture to extract the organic compound. After filtering, the volatiles were removed under reduced pressure, the residue was washed with n-pentane, and 1,3-didodecylbenzimidazolium bromide BI(2) was isolated as a white solid (21.1 g, yield: 93%).

$^1$H NMR (400 MHz, CDCl$_3$): δ 0.86 (t, 6H, CH$_3$), 1.10-1.50 (m, 36H, NCH$_2$CH$_2$(CH$_2$)$_9$CH$_3$), 2.05 (m, 4H, NCH$_2$Cl$_2$), 4.62 (t, 4H, NCH$_2$), 7.67 (m, 4H, Ar—H), 11.59 (s, 1H, NCHN). $^{13}$C NMR (100 MHz, CDCl$_3$): δ 14.13, 22.69, 26.59, 29.08, 29.33, 29.41, 29.52, 29.58, 29.60, 31.91, 47.74, 113.17, 127.18, 131.33, 142.75 ppm. HRMS calculated for C$_{31}$H$_{55}$N$_2$$^+$[M]$^+$: m/z=455.4365. found: 455.4360.

(Production of Supported Catalyst for Aldehyde Coupling Reaction)

The obtained benzimidazolium salt BI(2) and montmorillonite (Na-type montmorillonite) (hereinafter, referred to as "MMT") were subjected to a cation exchange reaction therebetween, to thereby obtain a supported catalyst comprising MMT having supported thereon an N,N-didodecylbenzimidazolium salt (hereinafter, referred to as MMT-BI(2)). Specifically, MMT (10 g, cation exchange capacity: 92.6 mequiv/100 g) and benzimidazolium salt BI(2) (7.44 g, 13.89 mmol), and methanol (200 mL) were placed in a 500 mL round bottom flask. The mixture was stirred vigorously at room temperature overnight. Then, the precipitate was filtered, washed with methanol, and dried at 70° C. under vacuum for 24 hours. To obtain the benzimidazolium salt BI(2) content in the resulting MMT-BI(2) catalyst, TGA was conducted with a heating rate of 10° C./min. from 20 to 900° C. under nitrogen atmosphere. From the TGA results of MMT alone and MMT-BI(2), the BI(2) content in the obtained MMT-BI(2) catalyst was calculated and found to be 533 μmol/g.

(Benzoin Condensation Reaction)

Furfural (0.166 mL, 2 mmol), THF (3 mL), the supported catalyst MMT-BI(2) (0.375 g, BI(2): 0.2 mmol), and oil-free NaH (4.8 mg, 0.2 mmol) were loaded into a 20 mL vial in the glovebox. The reaction mixture was stirred at room temperature in the glovebox for 6 hours. Then, 37% HCl (18 μL, 0.214 mmol) was added in the vial to quench the reaction. The in situ formed carbene was converted back into the benzimidazolium salt by reacting with HCl. Then, the vial was charged with 3 mL of methanol, and the resulting mixture was stirred overnight. It is presumed that this operation brought the benzimidazolium salt BI(2) detached from the interlayers of MMT into the interlayers. Then, from the resultant, the solid was filtered, washed with methanol, and dried at 70° C. overnight under vacuum. The recovered catalyst was reloaded into the 20 mL vial to catalyze the furfural coupling reaction under the same conditions as mentioned above. This process was repeated several times to evaluate the recyclability of the MMT-BI(2) catalyst. The reaction products were analyzed by $^1$H-NMR, and the furoin yields were obtained from the $^1$H-NMR spectra. The conditions and results are shown in Table 4.

Then, the reaction mixture was cooled to room temperature, and dry dichloromethane (30 mL) was added in the mixture to extract the organic compound. After filtering through celite, the solvents were removed under reduced pressure, and 1-dodecylbenzimidazole BI(3) was obtained as a beige viscous liquid (11.8 g, yield: 97%).

$^1$H NMR (400 MHz, CDCl$_3$): δ 0.87 (t, J=6.8 Hz, 3H, CH$_3$), 1.20-1.40 (m, 18H, NCH$_2$CH$_2$(CH$_2$)$_9$CH$_3$), 1.88 (m, 2H, NCH$_2$CH$_2$), 4.16 (t, J=7.2 Hz, 2H, NCH$_2$), 7.26-7.84 (m, 4H, Ar—H), 7.89 (s, 1H, NCHN). $^{13}$C NMR (100 MHz, CDCl$_3$): δ 14.16, 22.72, 26.85, 29.13, 29.36, 29.46, 29.55, 29.62, 29.84, 31.94, 45.13, 109.71, 120.35, 122.01, 122.79, 133.86, 142.94, 143.91 ppm. HRMS calculated for [C$_9$H$_{30}$N$_2$+H]$^+$ [M+H]$^+$: m/z=287.2487. found: 287.2491.

(Production of Supported Catalyst for Aldehyde Coupling Reaction)

The obtained 1-dodecylbenzimidazole BI(3) (25 mmol, 7.16 g) and a Merrifield's peptide resin (Aldrich, 200-400 mesh, extent of labeling: 3.5-4.5 mmol/g Cl$^-$ loading, 1% cross-linked with divinylbenzene) (3 g) were co-dispersed in acetonitrile (30 mL) in 250 mL three-necked round-bottom flask. The resulting mixture was stirred under reflux for 72 hours under nitrogen atmosphere. From the mixture, a reaction product of benzimidazole BI(3) and the crosslinked polystyrene (Resin-g-BI(3) catalyst) was filtered, washed with dichloromethane, and dried at 70° C. under vacuum overnight. Additionally, the filtrate was collected, the solvents were removed under vacuum, and ungrafted 1-dodecylbenzimidazole BI(3) (4.58 g) was recovered. Therefore, the content of BI(3) in the resulting Resin-g-BI(3) catalyst was found to be 1.614 mmol/g.

Further, the resulting Resin-g-BI(3) catalyst was characterized by FT-IR. In comparison between the obtained FT-IR spectrum of Resin-g-BI(3) with the FT-IR spectrum of the Merrifield's peptide resin, the FT-IR spectrum of Resin-g-BI(3) showed a new characteristic peak at 1558 cm$^{-1}$, which corresponded to the C=N vibration of imidazole ring. This result demonstrated that the Resin-g-BI(3) catalyst was successfully obtained.

(Aldehyde Coupling Reaction)

Furfural (0.384 g, 4 mmol). THF (6 mL), the Resin-g-BI(3) catalyst (BI(3): 0.4 mmol, 10 mol %) and a base (0.4 mmol, 10 mol %) shown in Table 4 were loaded into a 20 mL

TABLE 4

|  | Cycle of reaction | Catalyst | Catalyst loading (mol %) | NaH (mol %) | Solvent | Quenching agent | Acyloin yield (%) |
|---|---|---|---|---|---|---|---|
| Example 7 | 1 | MMT-BI(2) | 10 | 10 | THF | HCl/CH$_3$OH | 96.6 |
|  | 2 | Recycled | — | 10 | THF | HCl/CH$_3$OH | 96.1 |
|  | 3 | " | — | 10 | THF | HCl/CH$_3$OH | 96.1 |

As can be seen from Table 3, the furoin yields for all the three cycles remained at about 96%.

Examples 8 to 10

(Production of Benzimidazole BI(3))

A 250 mL three-necked round-bottom flask equipped with a stir bar and a condenser was charged with benzimidazole (5.00 g, 42.3 mmol) and oil-free NaH (1.02 g, 42.3 mmol). While stirring at 0° C. under nitrogen atmosphere, dry THF (30 mL) was slowly added into the flask. Then, the mixture was stirred at room temperature for 30 min. After that, dodecyl bromide (10.54 g, 42.3 mmol) was added to the mixture. The mixture was stirred at reflux for 24 hours.

vial in the glovebox. The resulting mixture was stirred under a nitrogen atmosphere at room temperature for 6 hours to perform a reaction. After the reaction, 37% HCl (36 μL, 0.428 mmol) was added to the vial to quench the reaction. Then, the solid catalyst was recovered from the reaction mixture, whereafter the recovered solid catalyst was filtered, washed several times with methanol, and dried at 70° C. under vacuum overnight. Then, the catalyst was reloaded into a 20 mL vial to catalyze the furfural self-coupling reaction under the same conditions as mentioned above. The reaction products were analyzed by $^1$H-NMR, and the furoin yields were obtained from the $^1$H-NMR spectra. The conditions and results are shown in Table 5.

TABLE 5

| | Cycle of Reaction | Catalyst (mol %) | Base (mol %) | Quenching agent | Furoin yield (%) | Average yield (%) |
|---|---|---|---|---|---|---|
| Example 8 | 1 | Resin-g-BI(3)/10 | Et$_3$N$^{1)}$/10 | | 12.3 | |
| Example 9 | 1 | Resin-g-BI(3)/10 | DRU/10 | HCl | 96.8 | 97.0 |
| | 2 | Recycled | DBU/10 | HCl | 96.9 | |
| | 3 | " | DBU/10 | HCl | 97.7 | |
| | 4 | " | DBU/10 | HCl | 97.0 | |
| | 5 | " | DBU/10 | HCl | 97.3 | |
| | 6 | " | DRU/10 | HCl | 96.7 | |
| | 7 | " | DBU/10 | HCl | 97.2 | |
| | 8 | " | DBU/10 | HCl | 97.1 | |
| | 9 | " | DBU/10 | HCl | 96.7 | |
| | 10 | " | DBU/10 | HCl | 97.1 | |
| Example 10 | 1 | Resin-g-BI(3)/10 | KO$^t$Bu$^{2)}$/10 | HCl | 96.5 | 96.6 |
| | 2 | Recycled | KO$^t$Bu/10 | HCl | 96.7 | |
| | 3 | " | KO$^t$Bu/10 | HCl | 96.5 | |
| | 4 | " | KO$^t$Bu/10 | HCl | 96.5 | |
| | 5 | " | KO$^t$Bu/10 | HCl | 96.5 | |
| | 6 | " | KO$^t$Bu/10 | HCl | 96.7 | |
| | 7 | " | KO$^t$Bu/10 | HCl | 96.6 | |
| | 8 | " | KO$^t$Bu/10 | HCl | 96.8 | |
| | 9 | " | KO$^t$Bu/10 | HCl | 96.9 | |
| | 10 | " | KO$^t$Bu/10 | HCl | 96.6 | |

Note:
[1]Et$_3$N means triethylamine.
[2]KO$^t$Bu means potassium tert-butoxide.

As shown in Table 5, in Example 8 where 10 mol % of Et$_3$N was used as the base, the furoin yield was very low, which was similar to the cases where the Silica-g-B(1) catalyst was used in combination with Et$_3$N (Examples 3 and 4). This result further verified that Et$_3$N is not so effective for deprotonating the benzimidazolium salt to form carbene under the reaction conditions employed. Nevertheless, when DBU or KO$^t$Bu was used as the base, excellent furoin yields (96.8% for Run 1 in Example 9, and 96.5% for Run 1 in Example 10) were achieved.

Furthermore, the recyclability of these catalyst systems was investigated. After the reaction, the in situ formed carbene was quenched with HCl, converting it back into benzimidazolium salt. The experimental results showed that in Example 9 where 10 mol % of DBU was used as the base, the furoin yields for all the ten cycles remained at about 97% (average yield: 97.0%). These results indicated that the Resin-g-BI(3) catalyst when used in combination with DBU could be recycled over ten times without changing its excellent catalytic activity. Similar results were observed in Example 10 where 10 mol % of KO$^t$Bu was used as the base.

These results were almost identical with those in Examples 1 to 6 where an inorganic carrier is used, further verifying that the carbene derived from a supported benzimidazolium salt with a long alkyl substituent exhibited outstanding catalytic performance and recyclability.

Comparative Examples 3 and 4

Production of Comparative Benzimidazolium Salt CE(1)

1-Methylimidazole (4.0 g, 48.7 mmol), (3-chloropropyl)triethoxysilane (17.6 g, 73.1 mmol) and dry acetonitrile (30 mL) were placed in a 250 mL three-necked round-bottom flask under nitrogen flow. The reaction mixture was stirred at reflux for 48 hours. Then, the mixture was cooled to room temperature, and the solvent was removed under reduced pressure. The excess (3-chloropropyl)triethoxysilane was extracted by dry diethyl ether, and the residue diethyl ether was removed under vacuum to give 1-methyl-3-(3-triethoxysilylpropyl) imidazolium chloride as a yellow viscous liquid (13.9 g, yield: 88%).

$^1$H NMR (400 MHz, CDCl$_3$): δ 0.59 (t, J=8.0 Hz, 2H, SiCH$_2$), 1.19 (t, J=7.2 Hz, 9H, Si(OCH$_2$CH$_3$)$_3$), 1.99 (m, 2H, NCH$_2$CH$_2$), 3.79 (q, J=7.2 Hz, 6H, Si(OCH$_2$CH$_3$)$_3$), 4.11 (s, 3H, N—CH$_3$), 4.31 (t, 2H, J=7.2 Hz, NCH$_2$), 7.29 (s, 1H, CH$_3$NCHCHN), 7.45 (s, 1H, CH$_3$NCHCHN), 10.73 (s, 1H, NCHN). $^{13}$C NMR (100 MHz, CDCl$_3$): δ 6.88, 18.00, 24.12, 36.27, 51.44, 58.30, 121.62, 123.75, 137.34 ppm. HRMS calculated for C$_{13}$H$_{27}$O$_3$SiN$_2^+$[M]$^+$: m/z=287.1791. found: 287.1785.

Production of Comparative Benzimidazolium Salt CE(2)

A 250 mL three-necked round-bottom flask equipped with a stir bar and a condenser was charged with benzimidazole (5.00 g, 42.3 mmol) and oil free NaH (1.02 g, 42.3 mmol) under nitrogen atmosphere. While stirring at 0° C., dry THF (30 mL) was slowly added into the flask. The mixture was stirred at room temperature for 30 minutes. Then, (3-chloropropyl)triethoxysilane (10.19 g, 42.3 mmol) was added, and the reaction mixture was stirred under reflux for 24 hours. The reaction mixture was cooled to room temperature, filtered through celite, and washed with dry dichloromethane. The filtrate was concentrated under reduced pressure, and yellow viscous liquid (1-(3-triethoxysilylpropyl) benzimidazole) was obtained which was used as such without any further purification.

To the resulting 1-(3-triethoxysilylpropyl) benzimidazole was added dry acetonitrile (30 mL) and methyl iodide (9.01 g, 63.5 mmol). The mixture was stirred at room temperature for 48 h under nitrogen atmosphere. The mixture was then evaporated to dryness under reduced pressure. The residue was washed with dry n-pentane and 1-(3-triethoxysilylpropyl)-3-methyl benzimidazolium iodide (17.7 g, 90%) was obtained as a yellow solid.

$^1$H NMR (400 MHz, CDCl$_3$): δ 0.71 (t, J=7.6 Hz, 2H, SiCH$_2$), 1.19 (t, J=7.2 Hz, 9H, Si(OCH$_2$CH$_3$)$_3$), 2.16 (m, 2H, NCH$_2$CH$_2$), 3.80 (q, J=7.2 Hz, 6H, Si(OCH$_2$CH$_3$)$_3$), 4.29 (s, 3H, NCH$_3$) 4.60 (t, J=7.6 Hz, 2H, NCH$_2$), 7.71 (m, 4H, Ar—H), 10.95 (s, 1H, NCHN). $^{13}$C NMR (100 MHz,

CDCl$_3$): δ 7.20, 18.22, 23.38, 34.32, 49.28, 58.54, 113.10, 127.26, 130.99, 131.90, 141.72 ppm. HRMS calculated for C$_{17}$H$_{29}$O$_3$SiN$_2$$^+$ [M]$^+$: m/z=337.1947. found: 337.1942.

Production of Comparative Supported Catalysts CE(1) and CE(2)

Comparative supported catalysts CE(1) and CE(2) were produced in the same manner as in Example 1 except that the comparative benzimidazolium salts CE(1) and CE(2) were used.

(Furfural Self-Coupling Reaction)

Using each of the comparative supported catalysts CE(1) and CE(2), a benzoin condensation reaction (coupling reaction of furfural) was performed in the same manner as in Example 1 and the reaction produces were analyzed in the same manner as in Example 1. The results are shown in Table 6.

(HMF Self-Coupling Reaction)

Using the comparative supported catalyst CE(2), a benzoin condensation reaction (coupling reaction of HMF) was performed in the same manner as in Example 6 and the reaction produces were analyzed in the same manner as in Example 6. The results are shown in Table 7.

TABLE 6

|  | Cycle of reaction | Catalyst (mol %) | Base (mol %) | Furoin yield (%) |
|---|---|---|---|---|
| Comparative Example 3 | 1 | CE(1) | Et$_3$N/10 | 0 |
|  | 2 | Recycled | DBU/10 | 2.9 |
|  | 3 | " | KO$^t$Bu/10 | 18.7 |
| Comparative Example 4 | 1 | CE(2) | Et$_3$N/10 | 0 |
|  | 2 | Recycled | DBU/10 | 74.4 |
|  | 3 | " | KO$^t$Bu/10 | 34.2 |

TABLE 7

|  | Cycle of reaction | Catalyst (mol %) | Base (mol %) | Time (h) | DHMF yield (%) | Average yield (%) |
|---|---|---|---|---|---|---|
| Comparative Example 4 | 1 | CE(2) | KO$^t$BU/10 | 24 | 7.4 |  |
|  | 2 | Recycled | DBU/10 | 24 | 34.2 |  |
|  | 3 | " | KO$^t$BU/20 | 24 | 29.6 |  |
|  | 4 | " | DBU/20 | 24 | 60.6 |  |

As can be seen from Tables 6 and 7, comparative catalysts CE(1) and CE(2) without a long-chain alkyl group were much inferior to the catalysts of the present invention for both coupling reactions of furfural and HMF.

What is claimed is:

1. A supported catalyst for aldehyde coupling reaction, comprising a carrier having supported thereon a catalyst comprising a benzimidazolium salt having, at a nitrogen atom thereof, a substituent selected from the group consisting of an aliphatic group having 6 or more carbon atoms and an aromatic group having 6 or more carbon atoms, the carrier comprising at least one substance selected from the group consisting of silica and clay.

2. The supported catalyst according to claim 1, wherein the carrier is silica.

3. The supported catalyst according to claim 1, wherein the carrier is clay.

4. A method for performing a coupling reaction between aldehyde molecules, comprising reacting aldehyde molecules in the presence of the catalyst according to claim 1 and a base, the aldehyde molecules each independently represented by the following formula (I):

R—CHO      (I)

wherein R represents a monovalent aliphatic group, a monovalent aromatic group or a monovalent heterocyclic aromatic group.

5. The method according to claim 4, wherein the monovalent aromatic group is an unsubstituted or substituted phenyl group and the monovalent heterocyclic aromatic group is an unsubstituted or substituted furyl group.

6. The method according to claim 4, wherein the base is selected from the group consisting of tertiary amines, alkoxides, metal hydroxides, metal hydrides, carbonate salts, phosphate salts and cyclic amidines.

7. The method according to claim 4, wherein the base is selected from the group consisting of potassium tert-butoxide, 1,8 diazabicyclo[5.4.0]undec-7-ene, and sodium hydride.

8. A method for regenerating the supported catalyst of claim 1, comprising treating the supported catalyst used for aldehyde coupling reaction with an acid.

9. The supported catalyst according to claim 1, wherein the benzimidazolium salt has, at a nitrogen atom thereof, an aromatic group having 6 or more carbon atoms.

10. The supported catalyst according to claim 1, which is in the form of a mixture with a base selected from the group consisting of potassium tert-butoxide, 1,8 diazabicyclo[5.4.0]undec-7-ene, and sodium hydride.

* * * * *